(12) United States Patent
Laviola et al.

(10) Patent No.: US 12,324,604 B2
(45) Date of Patent: Jun. 10, 2025

(54) LOCALIZATION DEVICE FOR INSERTING LOCALIZER AND METHODS OF INSERTION

(71) Applicant: HOLOGIC, INC., Marlborough, MA (US)

(72) Inventors: John Laviola, Marlborough, MA (US); Kenneth F. Defreitas, Marlborough, MA (US); Andrew L. Jagenow, Marlborough, MA (US)

(73) Assignee: Hologic, Inc., Marlborough, MA (US)

( * ) Notice: Subject to any disclaimer, the term of this patent is extended or adjusted under 35 U.S.C. 154(b) by 1007 days.

(21) Appl. No.: 17/280,372

(22) PCT Filed: Sep. 23, 2019

(86) PCT No.: PCT/US2019/052411
§ 371 (c)(1),
(2) Date: Mar. 26, 2021

(87) PCT Pub. No.: WO2020/068658
PCT Pub. Date: Apr. 2, 2020

(65) Prior Publication Data
US 2021/0378704 A1 Dec. 9, 2021

Related U.S. Application Data

(60) Provisional application No. 62/737,203, filed on Sep. 27, 2018.

(51) Int. Cl.
*A61B 17/34* (2006.01)
*A61B 17/00* (2006.01)
*A61B 90/00* (2016.01)

(52) U.S. Cl.
CPC ...... *A61B 17/3421* (2013.01); *A61B 17/3468* (2013.01); *A61B 90/39* (2016.02);
(Continued)

(58) Field of Classification Search
CPC . A61B 90/39; A61B 17/3421; A61B 17/3468; A61B 2090/3908; A61B 2090/3925; A61B 2090/3987
See application file for complete search history.

(56) References Cited

U.S. PATENT DOCUMENTS

| 2002/0059938 A1 | 5/2002 | Fogarty et al. |
| 2016/0279423 A1* | 9/2016 | Kelly ............... A61M 25/0136 |
| 2017/0119492 A1 | 5/2017 | Chesbrough |

FOREIGN PATENT DOCUMENTS

| EP | 2 080 487 A1 | 7/2009 |
| WO | 2005/120628 A2 | 12/2005 |
| WO | 2010/077244 A1 | 7/2010 |

OTHER PUBLICATIONS

International Search Report and Written Opinion of the International Searching Authority for International Patent Application No. PCT/US2019/052411 mailed Feb. 11, 2020, 19 pages.
(Continued)

*Primary Examiner* — Chao Sheng
(74) *Attorney, Agent, or Firm* — Merchant & Gould P.C.

(57) ABSTRACT

A cannula defines a cannula axis and extends from the body of a localization device. An actuation system and a control rod are slidably and rotatably disposed within the body and the cannula. The control rod is operatively coupled to the actuation system for both slidable actuation and rotatable actuation.

19 Claims, 15 Drawing Sheets

(52) U.S. Cl.
CPC ............... *A61B 2017/00389* (2013.01); *A61B 2090/3908* (2016.02); *A61B 2090/3925* (2016.02); *A61B 2090/3987* (2016.02)

(56) References Cited

OTHER PUBLICATIONS

PCT International Preliminary Report on Patentability in International Application PCT/US2019/052411, mailed Apr. 8, 2021, 11 pages.

\* cited by examiner

LOCALIZATION DEVICE FOR INSERTING LOCALIZER AND METHODS OF INSERTION

CROSS-REFERENCE TO RELATED APPLICATIONS

This application is a National Stage Application of PCT/US2019/052411, filed Sep. 23, 2019, which claims priority to and the benefit of U.S. Provisional Patent Application No. 62/737,203, filed Sep. 27, 2018, the disclosures of which are hereby incorporated by reference herein in their entireties. To the extent appropriate, a claim of priority is made to each of the above disclosed applications.

BACKGROUND

Identifying the location of breast cancer lesions, such as tumors, prior to subsequent surgical removal is a useful but difficult task. Proper localization of a lesion allows a surgeon to more accurately perform the surgical procedure by removing the entire lesion without unnecessarily removing healthy tissue. Most commonly, lesions are localized for surgery by inserting a localization element that may be in the form of a hook and be connected to one or more stainless steel wires that are used to aid in locating the hooked localization element in in a later procedure. The hooked localization element is secured to and/or around the lesion. Generally, an interventional radiologist deploys the localization element with a localization device under an imaging modality such as x-ray or ultrasound prior to surgery, such that the wire(s) extend from the breast after localization element insertion. During subsequent surgery the surgeon uses the wire(s) as a guide to locate the hook of the localization element, and thus the lesion. The surgeon then removes the lesion and the localization element in their entireties.

It is with respect to these and other general considerations that the aspects disclosed herein have been made. Also, although relatively specific problems may be discussed, it should be understood that the examples should not be limited to solving the specific problems identified in the background or elsewhere in this disclosure.

SUMMARY

Examples of the present disclosure describe systems and methods for the localization of an implanted marker through ultrasound technology along with additional combinations of other modalities.

In an aspect, the technology relates to a localization device having: a body; a cannula extending from the body, wherein the cannula defines a cannula axis; an actuation system; and a control rod slidably and rotatably disposed within at least one of the body and the cannula, wherein the control rod is operatively coupled to the actuation system for both slidable actuation and rotatable actuation. In an example, the localization device has a localizer releasably coupled to the control rod, wherein the localizer is configured to slide along the cannula axis due to a sliding movement of the control rod, and wherein the localizer is configured to rotate relative to the cannula axis due to a rotating movement of the control rod. In another example, the localizer includes a localization element and a wire coupled to the localization element, wherein the wire is disposed at least partially within the control rod. In yet another example, the localization device has a coupler connecting the localization element to the wire. In still another example, at least a portion of the wire is coiled within the body.

In another example of the above aspect, the actuation system has a slidable actuator and a rotatable actuator. In an example, the slidable actuator is discrete from the rotatable actuator. In another example, the rotatable actuator is slidably connected to the control rod at a spline.

In another aspect, the technology relates to a localization device having: a body; a cannula extending from the body, wherein the cannula defines a cannula axis; an actuation system connected to the body, wherein the actuation system includes a wire latch; a localization element responsively coupled to the actuation system and configured for movement about the cannula axis and along the cannula axis; and a wire coupled to the localization element, and wherein the wire is releasably coupled to the wire latch. In an example, the actuation system includes a control rod movably disposed within at least one of the body and the cannula. In another example, the actuation system is adapted for a rotational movement and a sliding movement. In yet another example, the actuation system has a rotatable actuator and a slidable actuator. In still another example, the rotatable actuator is discrete from the slidable actuator.

In another example of the above aspect, the actuation system is positionable in a first position and a second position, and wherein the latch is configured to disengage from the wire when the actuation system is in the second position. In an example, when in the second position, the localization element is fully extended from the cannula.

In another aspect, the technology relates to a method of inserting a localizer with an insertion device containing the localizer, the method including: inserting a cannula and the localizer into a tissue of a patient, wherein the cannula has a cannula axis, and wherein the localizer is disposed at least partially within the cannula; rotating the localizer about the cannula axis while holding the cannula in a substantially rotationally static position; sliding the localizer along the cannula axis while holding the cannula in a substantially slidingly static position; and withdrawing the cannula from the tissue such that the localizer remains within the tissue. In an example, the method further includes releasing the localizer from a latch disposed within the insertion device, prior to withdrawing the cannula. In another example, the method further includes restraining a position of the latch within the insertion device. In yet another example, releasing the localizer and restraining the position of the latch is performed substantially simultaneously. In still another example, rotating the localizer is performed prior to sliding the localizer.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Additional aspects, features, and/or advantages of examples will be set forth in part in the description which follows and, in part, will be apparent from the description, or may be learned by practice of the disclosure.

BRIEF DESCRIPTION OF THE DRAWINGS

Non-limiting and non-exhaustive examples are described with reference to the following figures.

DETAILED DESCRIPTION

The localization devices described herein include features that lessen complexities of localization element insertion. From the beginning of an insertion procedure to the end, the localization device may be used with one hand, leaving the other hand free to operate the ultrasound probe or other imaging system, or to otherwise manipulate the breast. That is, the localization device may be inserted into the breast tissue and manipulated without the need for the surgeon to change the grip on the device, uncomfortably position her hand, etc. The localization device is used to insert a localizer which marks a lesion or region of interest. The localizer is constructed so as to interact with components of the localization device so as to be extended from, retracted into, and released from the localization device, without requiring more than one-handed operation of the localization device. Further, prior to insertion, the localization element (and associated components as described below) are contained within the localization device, thus reducing the likelihood of damage to the localization element, contamination thereof, and/or complexity of use. Further features of the localization devices described herein enable further manipulations of the localization element prior to and during insertion thereof.

Figure 1A:
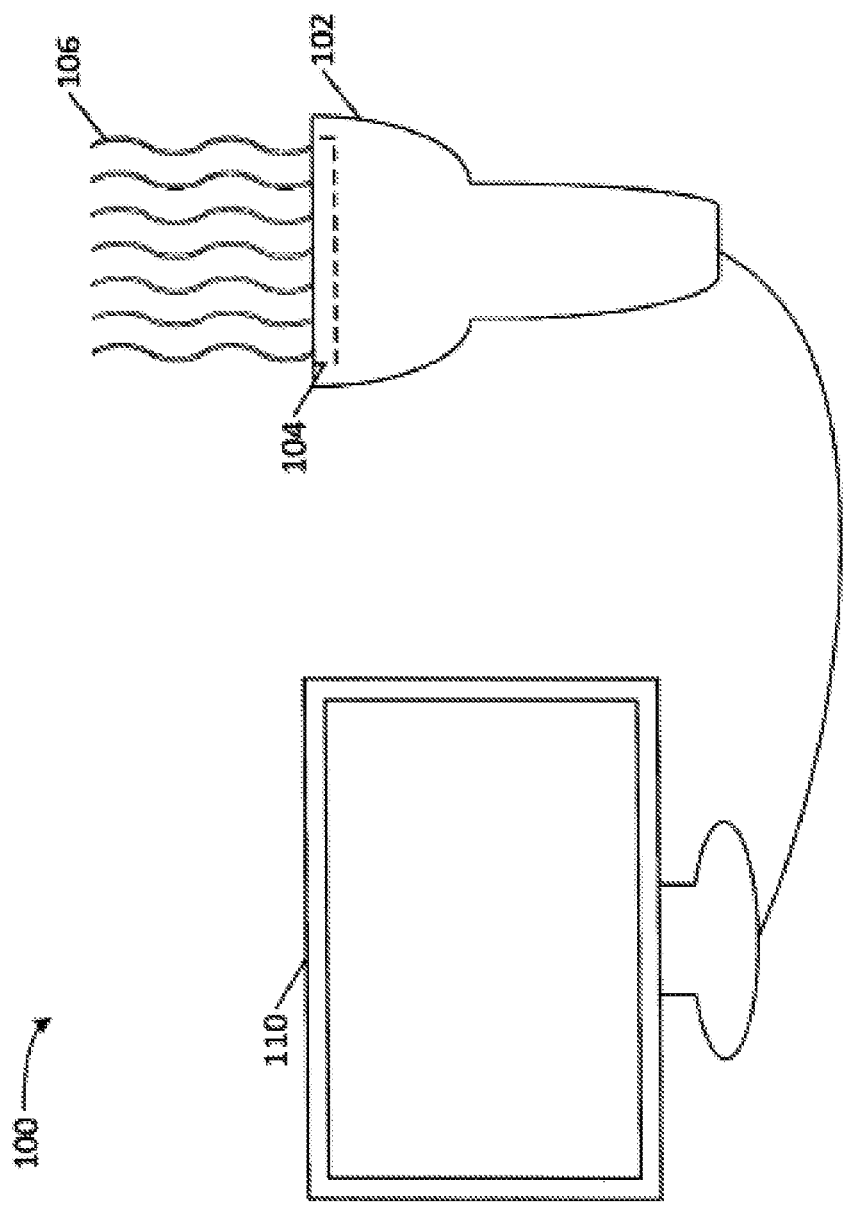
FIG. 1A depicts an example of an ultrasound system.

FIG. 1A depicts an example of an ultrasound system 100. The ultrasound system 100 includes an ultrasound probe 102 that includes an ultrasonic transducer 104. The ultrasonic transducer 104 is configured to emit an array of ultrasonic sound waves 106. The ultrasonic transducer 104 converts an electrical signal into ultrasonic sound waves 106. The ultrasonic transducer 104 may also be configured to detect ultrasonic sound waves, such as ultrasonic sound waves that have been reflected from internal portions of a patient. In some examples, the ultrasonic transducer 104 may incorporate a capacitive transducer and/or a piezoelectric transducer, as well as other suitable transducing technology. Various embodiments describe a localization device and an associated localizer. The localization device is deployed to the lesion or region of interest under an imaging modality, a procedure typically referred to as a localization procedure. For clarity, a localization procedure utilizing ultrasound as the imaging modality is described in FIGS. 1A-1B, and generally elsewhere herein. However, any modality, such as X-ray or MRI, may be used during the localization procedure.

The ultrasonic transducer 104 is also operatively connected (e.g., wired or wirelessly) to a display 110. The display 110 may be a part of a computing system, including processors and memory configured to produce and analyze ultrasound images. The display 110 is configured to display ultrasound images based on an ultrasound imaging of a patient. The ultrasound imaging performed in the ultrasound localization system 100 is primarily B-mode imaging, which results in a two-dimensional ultrasound image of a cross-section of a portion of the interior of a patient. The brightness of the pixels in the resultant image generally corresponds to amplitude or strength of the reflected ultrasound waves. Other ultrasound imaging modes may also be utilized.

Figure 1B:
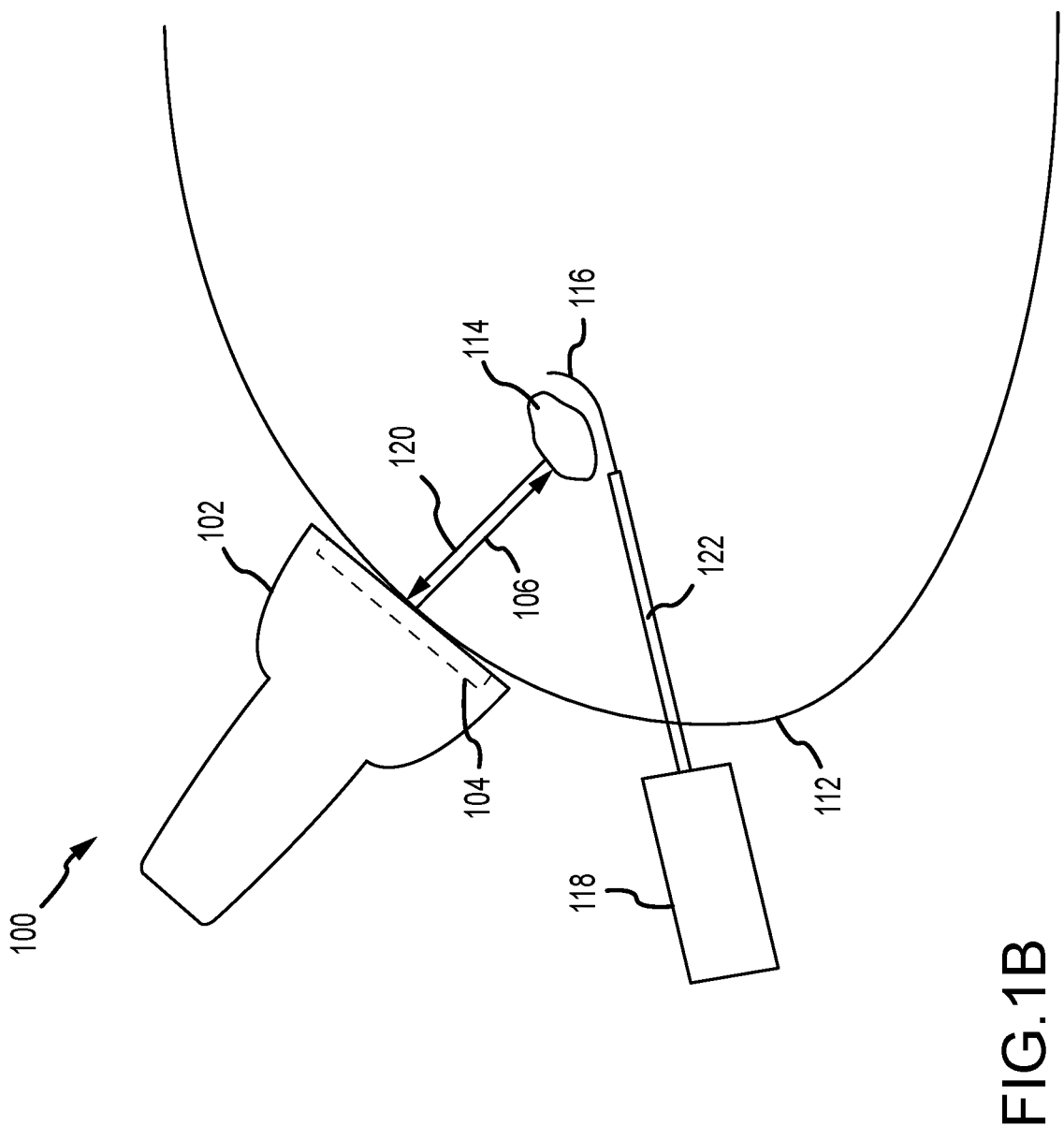
FIG. 1B depicts an example of the ultrasound system in use with a patient.

FIG. 1B depicts an example of the ultrasound system 100 in use with a patient 112. The ultrasound probe 102 is in contact with a portion of the patient 112, such as a breast of the patient 112. In the position depicted in FIG. 1B, the ultrasound probe 102 is being used to image a portion of the patient 112 containing a lesion 114. The ultrasound probe 102 is typically held in one hand of a radiologist. A localization device 118 is held in the other hand. The localization device 118 includes a cannula 122 extending therefrom. The cannula 122 is inserted into the breast 112 and guided by the ultrasound imaging to the lesion. A localization element 116 is extended from the cannula 122 and implanted at the lesion 114. The localization element 116 allows for the lesion 114 to be localized or marked, and is used during the subsequent surgical procedure to physically locate the lesion, since the surgical procedure is not performed with the use of imaging.

To image the portion of the patient 112 containing the localization element 116, the ultrasonic transducer 104 emits an array of ultrasonic sound waves 106 into the interior of the patient 112. A portion of the ultrasonic sound waves 106 are reflected off internal components of the patient 112 as well as the localization element 116, when the localization element 116 is in the field of view, and return to the ultrasound probe 102 as reflected ultrasonic sound waves 120. The reflected ultrasonic sound waves 120 may be detected by the ultrasonic transducer 104. For instance, the ultrasonic transducer 104 receives the reflected ultrasonic sound waves 120 and converts the ultrasonic sound waves 120 into an electric signal that can be processed and analyzed to generate ultrasound image data on display 110. The depth of the localization element 116 or other objects in an imaging plane may be determined from the time between a pulse of ultrasonic waves 106 being emitted from the ultrasound prove 102 and the reflected ultrasonic waves 120 being detected by the ultrasound probe 102. For instance, the speed of sound is well-known and the effects of the speed of sound based on soft tissue are also determinable. Accordingly, based on the time of flight of the ultrasonic waves 106 (more specifically, half the time of flight), the depth of the object within an ultrasound image may be determined. Other corrections or methods for determining object depth, such as compensating for refraction and variant speed of waves through tissue, may also be implemented. Those having skill in the art will understand further details of depth measurements in medical ultrasound imaging technology.

In addition, multiple frequencies or modes of ultrasound techniques may be utilized. For instance, real time and concurrent transmit and receive multiplexing of localization frequencies as well as imaging frequencies and capture frequencies may be implemented. The localization frequencies may be implemented for lesion or marker targeting and the imaging frequencies implemented for ultrasonography. Utilization of these capabilities provide information to co-register or fuse multiple data sets from the ultrasound techniques to allow for a real-time visualization of a localization element 116 and medical images on the display 110. The imaging frequencies and capture sequences may include B-mode imaging (with or without compounding), Doppler modes (e.g., color, duplex), harmonic mode, shearwave and other elastography modes, and contrast-enhanced ultrasound, among other imaging modes and techniques.

In the example depicted, the portion of the localization element 116 proximate the lesion may have a curled, curved, or hooked shape so as to secure the element 116 to or about the lesion. Other configurations, such as double hooks or coils may also be utilized. The localization element 116 may also be made from a material that makes the localization element 116 easier to detect within the ultrasound image 130 or image data. For instance, the material of the localization element 116 may be selected to be a material that has a high degree of echogenicity. By forming the localization element 116 of a material having a higher degree of echogenicity, the localization element 116 will appear brighter in the resulting ultrasound image as materials with higher degrees of echogenicity have a higher ability to reflect ultrasound waves. In some examples, incorporating air or other gases into the localization element 116 or portions thereof may cause the localization element 116 to appear brighter in the ultrasound image 130. In other examples, the localization element 116 may include a material that is capable of converting the ultrasonic sound wave energy into light in the visible spectrum.

The localization element 116 may be constructed to provide additional indicators to assist the surgeon in finding the localization element 116. For example, the localization element 116 may include luminescent materials that emit visible light so the surgeon can see the localization element 116 during a subsequent surgery. In additional examples, the different portions of the localization element 116 may be distinguishable from one another based on sandblasting, patterning, numbering, lettering, or other features that may be able to be distinguished in a resultant image. The numbering, patterning, lettering, etc. may be raised, embossed, or made of a different material to cause the markings to be more visible in an image taking during insertion, or even a subsequent image, if desired. Localization elements made from distinct combinations of radiolucent or radiopaque materials may also be employed so as to create a distinct visual appearance in, e.g., an x-ray image. Manufacturing techniques and materials utilized in localization elements 116 so as to improve visibility in x-ray, MRI, ultrasound, or other imaging modalities are also contemplated.

Once appropriately implanted, the localization device 118 may be pulled away from the breast 112, such that the cannula is removed from the breast tissue. The localization element 116 remains proximate the lesion and a wire (not shown) that is fixed to the localization element 116 prior to insertion extends out of the breast 112. The wire may be held in place against the skin with tape or gauze and the patient may leave the implantation location. During a subsequent surgery procedure, the wire acts as a guide for the surgeon to locate and access the lesion 114 and to remove it, while leaving healthy tissue intact.

Figure 2A:
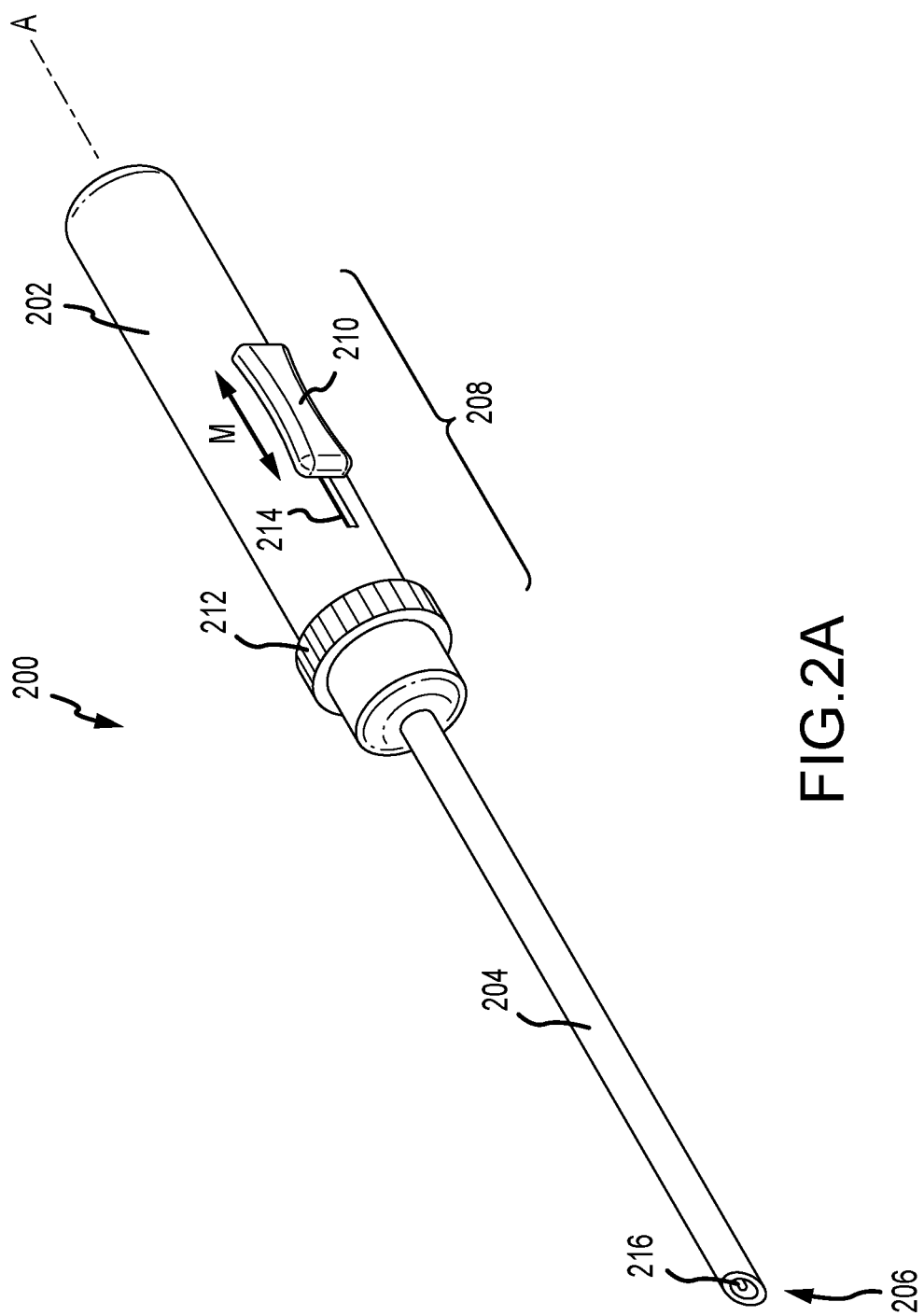
FIGS. 2A-2C depict perspective views of an example of a localization device, at various stages of localizer insertion.
Figure 2B:
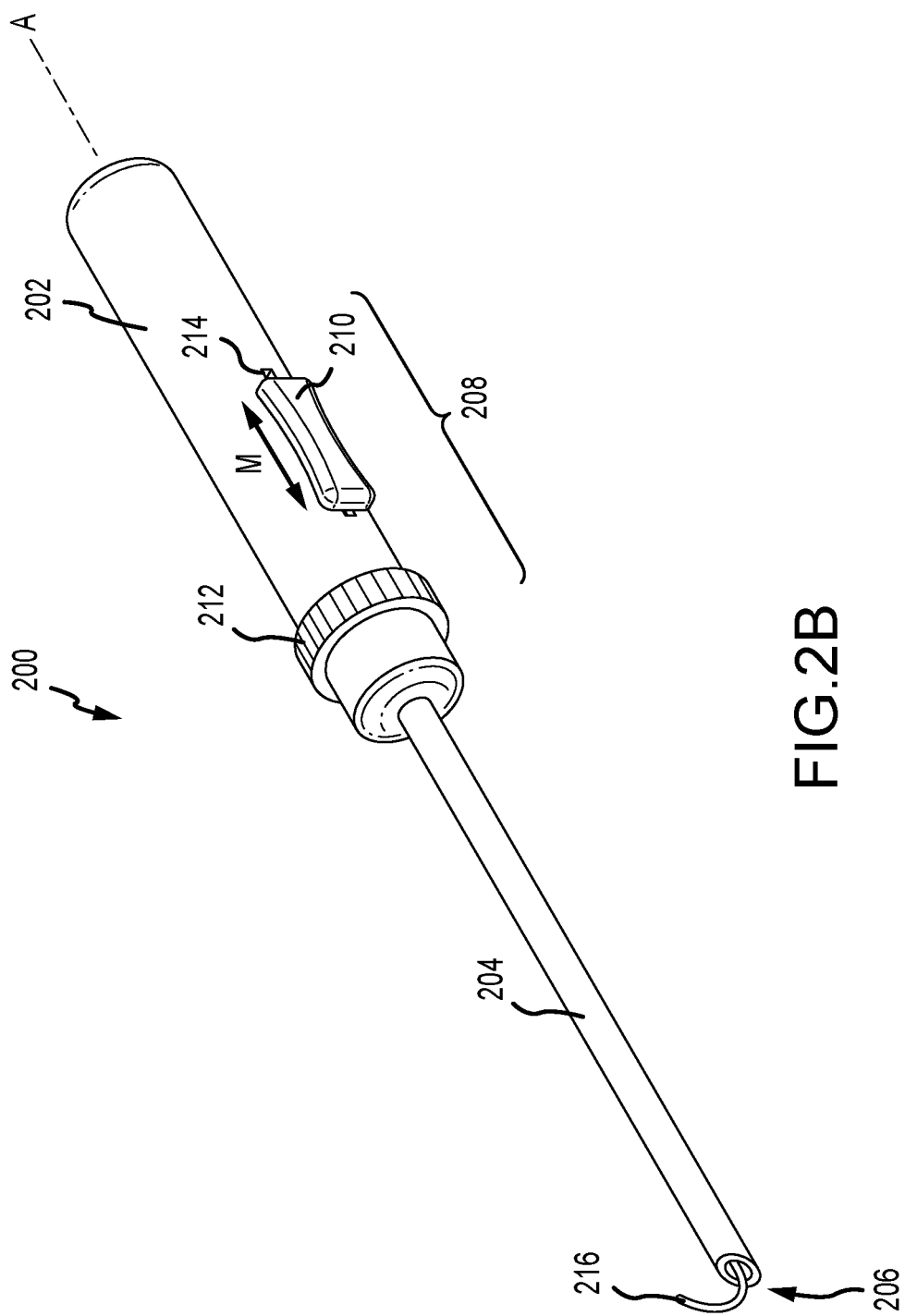
Figure 2C:
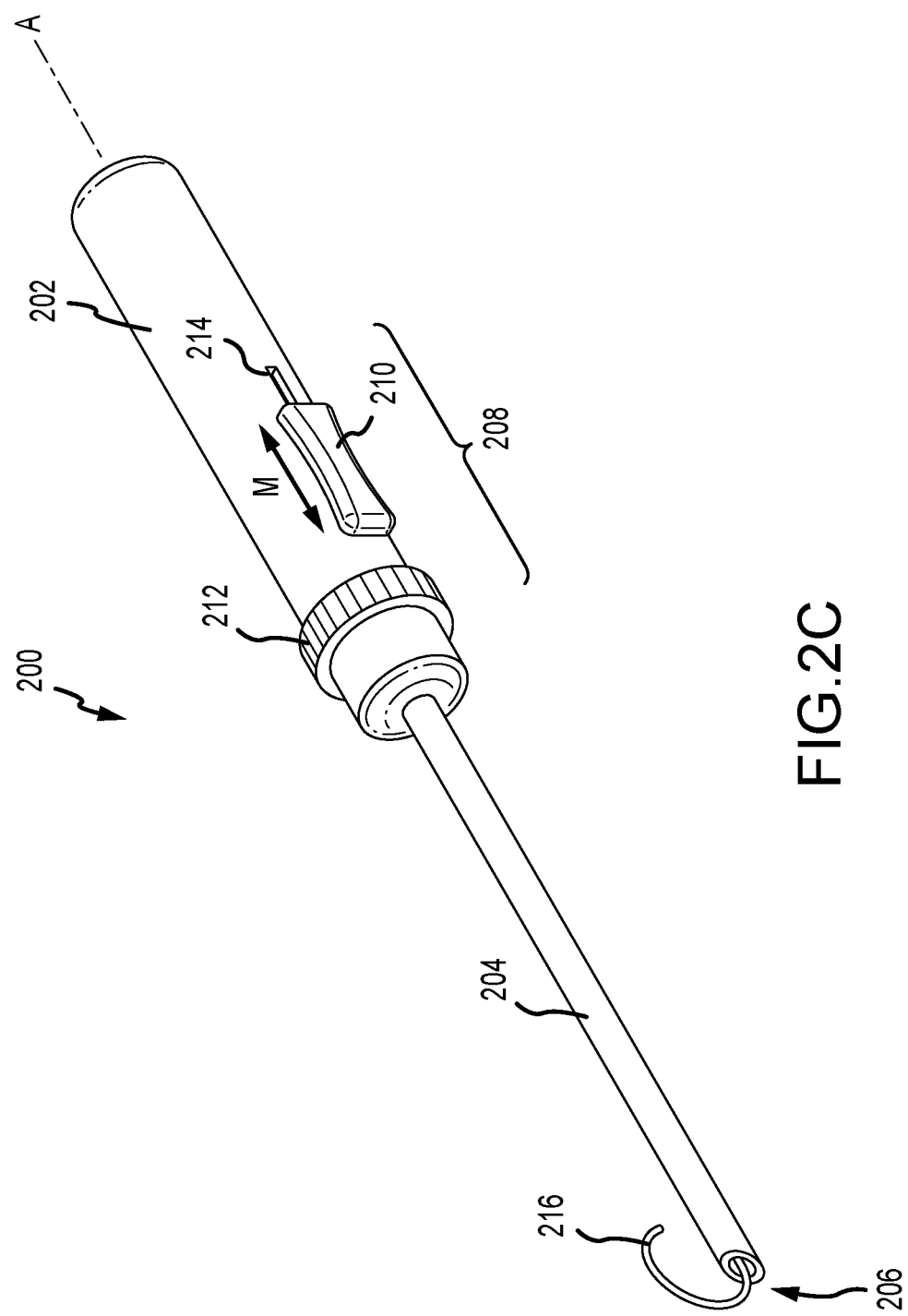

FIGS. 2A-2C depict perspective views of an example of a localization device 200, at various stages of localization element 216 insertion. FIGS. 2A-2C are described concurrently. The device 200 includes a handle or body 202, which is elongate and sized to be gripped in one hand and a localization element 216 disposed within. A user manipulates the body of the device 200 to release or deploy the localization element 216 inside the breast, with the localization element 216 placed at or inside the lesion. The body 202 may be formed of a rigid plastic that may be smooth, easy to grip, cleanable or otherwise able to be sanitized. Polycarbonates, acrylics, polypropylenes, and other medical grade plastics may be utilized. A cannula 204 extends from the body 202 such that the cannula 204 and body 202 define a common elongate axis A. The cannula 204 includes a tip 206 that is angled for penetration of tissue. Typically, the cannula 204 may be formed from a rigid medical grade metal such as stainless steel, titanium, etc. The localization device 200 also includes an actuation system 208, two actutable components of which are depicted. These include a slidable actuator 210 and a rotatable actuator 212. The slidable actuator 210 is disposed so as to slide along the length of a slot 214 defined by the body 202. The slidable actuator 210 may include a shaped, knurled, or otherwise textured element that may be actuated by a user's thumb or finger. In an example, the slidable actuator 210 may include a recess or other feature enabling at least partial insertion of the finger or thumb allowing better grip and control of the actuator 210. In general, however, a slightly concave element having a low central region and higher ends that is also knurled to increase friction against the thumb is sufficient. The rotatable actuator 212 is a generally ring-shaped element that substantially surrounds the body 202. Like the slidable actuator 210, the rotatable actuator 212 may be knurled or otherwise textured to increase frictional contact with the thumb or finger. Other components of the actuation system 208 are described herein.

In general, the actuation system 208 is utilized to advance, retract, and/or otherwise move and manipulate the localization element 216 contained within the localization device 200 prior to release of the localization element 216. In FIGS. 2A-2C, only the localization element 216 is depicted. The localization element 216 may be in the form of a shape-memory allow that forms a curved or hooked element when released from the cannula 204. As described in FIG. 3 below, the localization element 216 forms one portion of a localizer (which may include also a coupler and one or more wires), which is used to mark and locate the lesion or region of interest. The distance that the localization element 216 extends out of the tip 206 of the cannula 204 corresponds generally to the position of the slidable actuator 210 along its range of motion M, which is bounded by the limits of a slot 214. Although the element 216 is depicted as having a significantly smaller size than the tip 206 of the cannula 204, the element 216 may be sized or configured to more effectively close off the opening of the tip 206, thus limiting the potential of tissue intrusion therein during insertion. In another example, a cannula/trocar assembly, as known in the art, may first be introduced into the breast tissue, prior to insertion of the cannula 206.

Figure 3:
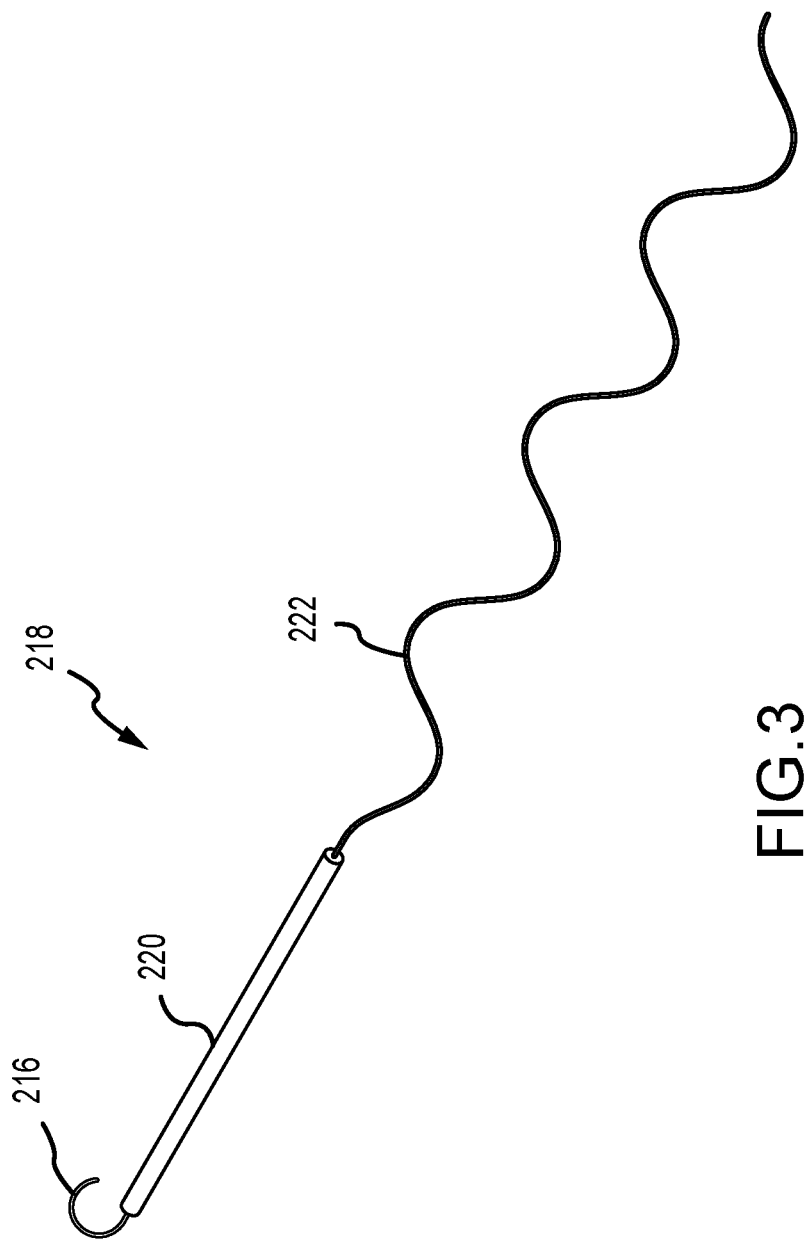
FIG. 3 depicts a localizer in accordance with one example of the present technology.

FIG. 3 depicts a localizer 218 that is inserted into the breast tissue. The localizer 218 includes a localization element 216, a rigid coupler 220, and a wire 222. The localization element 216 may be formed of nitinol or other material that may perform as described herein. Certain performance features, such as visibility under ultrasound or other imaging modalities, shape memory, etc., may be desirable for the localization element 216. The localization element 216 is connected to the wire 222 either directly or at the coupler 220. The coupler 220 provides an interface with the internal components of the localization device to allow for controlled manipulation of the entire localizer 218, even though few components thereof are amenable to such manipulations. That is, the localization element 216 has a predetermined bias (e.g., due to its manufacture from shape-memory material) that may resist manipulation and cause damage to the localization element 216. Similarly, the wire 222 is manufactured of extremely flexible material (e.g., for patient comfort after insertion) that makes rotation or pushing or pulling thereof extremely difficult. Further, the coupler 220 forms a point of connection between the two differently-constructed and performing materials of the localization element 216 and the wire 222.

In examples, the coupler 220 may be integrally formed with the localization element 216, or may be joined thereto with one or more fastening systems 226. Such systems may include welds, brazes, adhesives, frictional engagement elements, mechanical fasteners, or combinations thereof. In this case, the coupler 220 is a substantially rigid material that has a predetermined length $L_c$. The length $L_c$ may be about 2 cm, about 2.25 cm, or about 1.75 cm, although other lengths are contemplated. The first end of the wire 222 is connected to the coupler 220, for example, with one or more fastening systems 226 as described above in the context of the localization element 216 and coupler 220. Here, the fastening system 226 is a pin about which a first end of the wire 222 is secured. The coupler 220 provides a rigid structure that allows the localization element 216 to be advanced within and from the cannula 204 (and otherwise be manipulated) by the actuation system 208, as described in more detail below. Additionally, the coupler 220 allows a surgeon to determine a distance from the localization element 216 during a subsequent surgical procedure. As the surgeon follows the wire 222 from the exterior of the breast, the coupler 220 is encountered prior to the localization element 216. Since the coupler 220 is of a known predetermined length $L_c$, the surgeon knows her position relative to the localization element 216 and may take further actions or preparation as necessary prior to encountering the localization element 216 and lesion. Such actions may include actuating suction (if utilized), increasing a size of the penetration, etc.

Figure 3A:
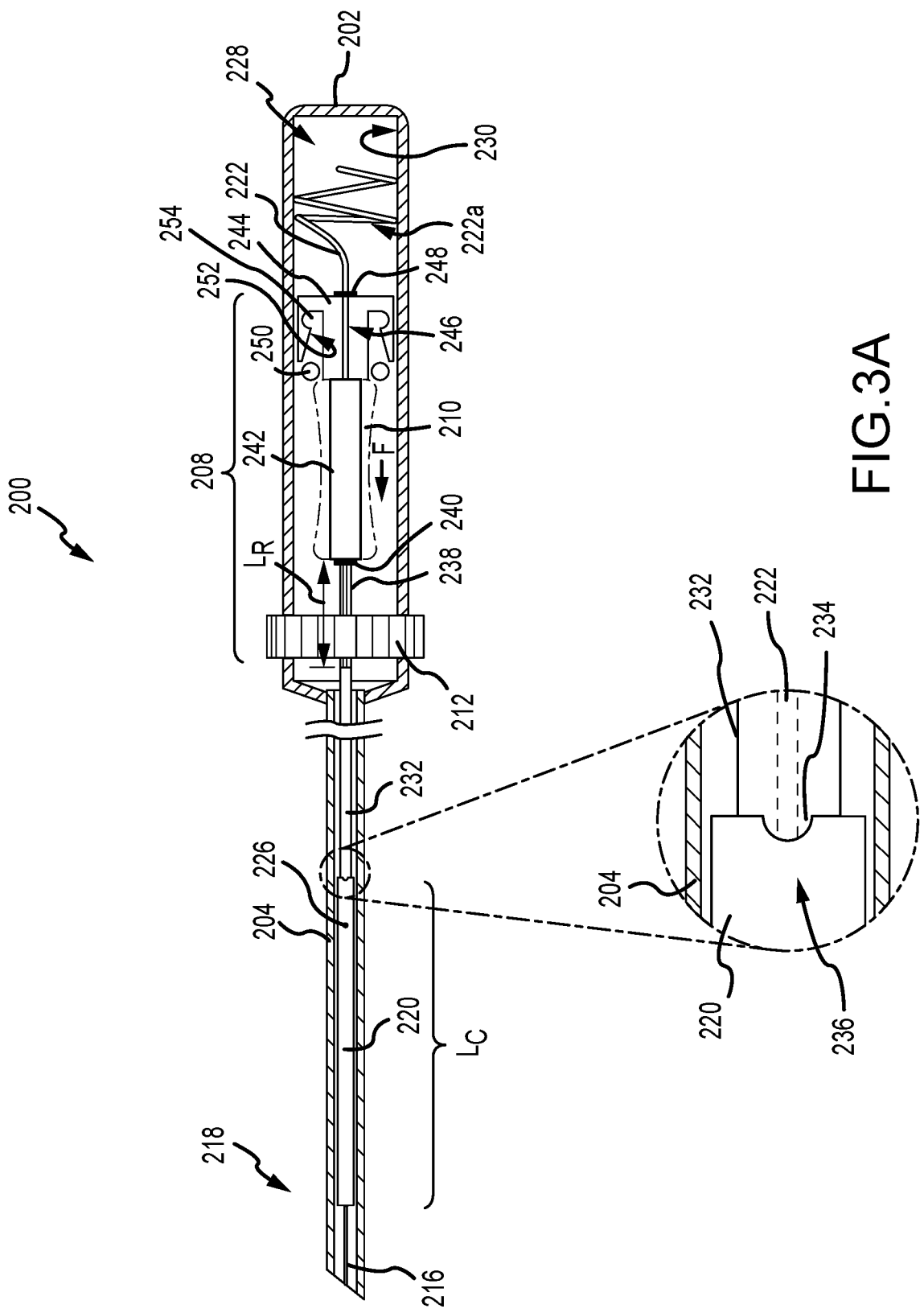
FIGS. 3A-3C depict partial side cut-away views of the localization device of FIGS. 2A-2C being used during an insertion procedure of the localizer of FIG. 3.
Figure 3B:
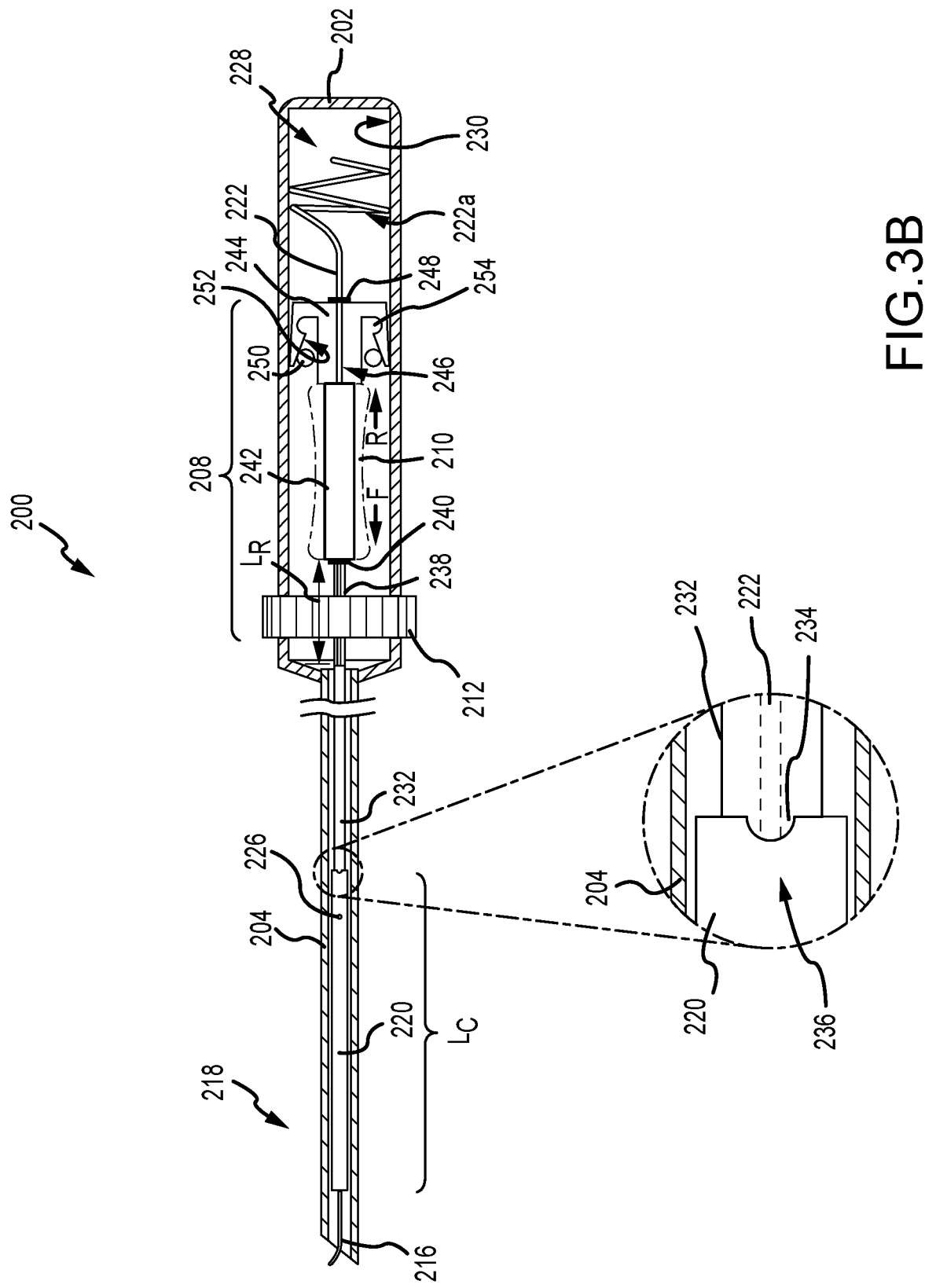
Figure 3C:
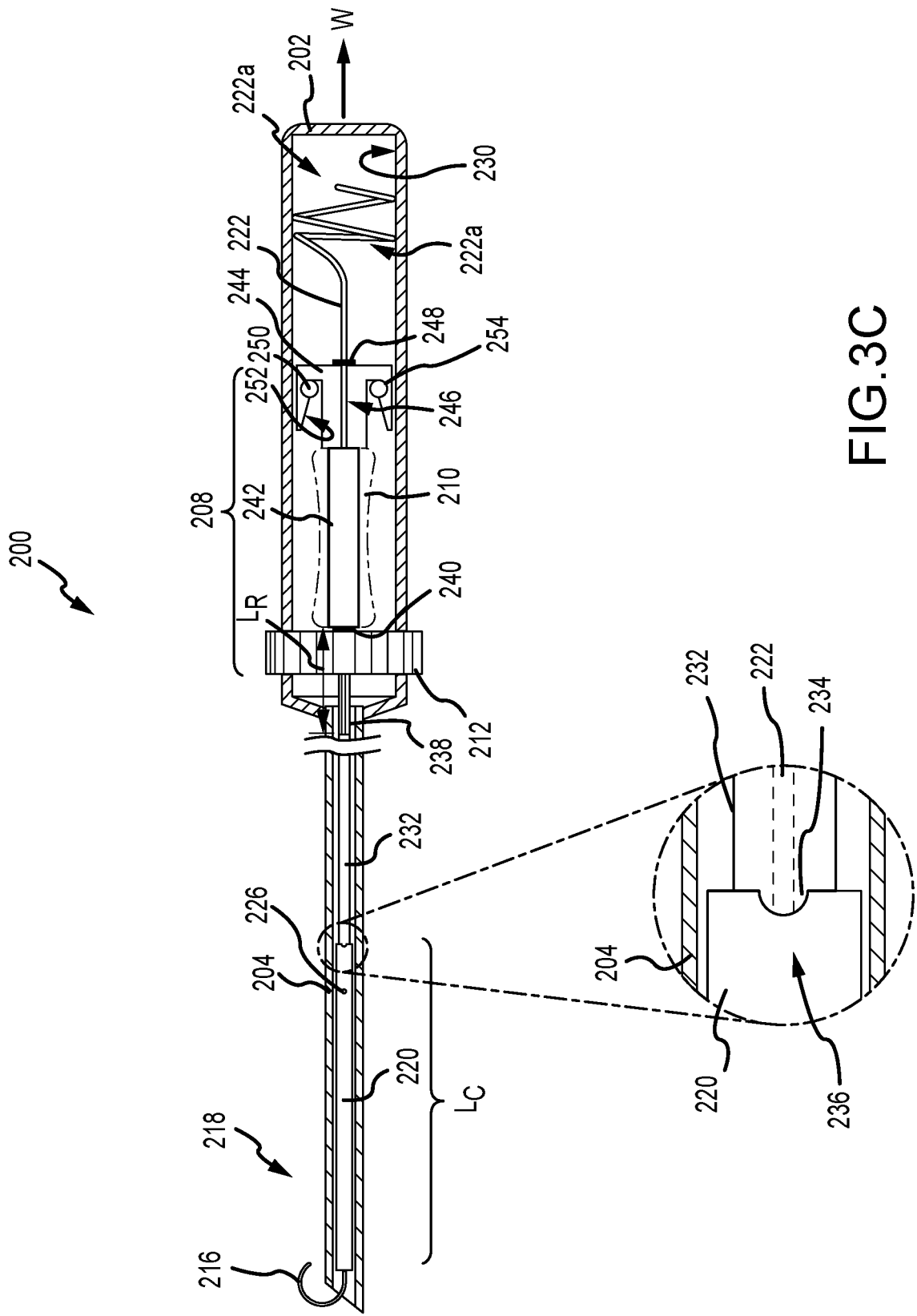

FIGS. 3A-3C depict the localization device 200 of FIGS. 2A-2C during various stages of localization element 216 insertion. Several of the exterior components are depicted as transparent so as to depict internal components. FIG. 3A depicts a first stage of insertion, where the localization element 216, coupler 220, and wire 222 are contained within the localization device 200. A second end 222a of the wire 222 is disposed within a wire chamber 228 defined by the body 202. The second end 222a of the wire 222 may be freely coiled within the wire chamber 228 or may be wound about a spool. In another example, an inner wall 230 of the wire chamber 228 may be formed with a plurality of channels (not shown) in which the second end 222a of the wire 222 may be arranged. Use of a spool, channels, or a free coil may allow for a controlled unravelling and raveling of the second end of the wire 222a, as the localization element 216 is positioned within the body 202. Containing the second end of the wire 222a within the wire chamber 228 may help maintain sterilization of the wire 222, unlike prior art devices where a portion of the wire extends out of an end of the handle. Such prior art configurations were generally required to retract the localization element (by gripping and pulling the free end of the wire) if it was extended in an undesirable orientation or location. The configuration of the present localization device 200, which allows for retraction of the localization element 216 without the need for gripping of the wire 222 by the surgeon, obviates the need for such a configuration.

In addition to the slidable actuator 210 and the rotatable actuator 212, the actuation system 208 includes several components that enable manipulation and implantation of the localization element 216. A hollow control rod 232 is disposed within the cannula 204. A first end of the control rod 232 includes a key 234 that is engaged with the coupler 220 at a slot 236 or other feature. One or more splines 238 are disposed along a spline length LR of the control rod 232. The spline length LR corresponds generally to the maximum range of motion of the slidable actuator 210, such that the rotatable actuator 212 can maintain engaging contact with the spline 238 at any location along that range of motion. The slidable actuator 210 is fixed to a carriage 242, which slides linearly within the body 202. The carriage 242 is engaged with the control rod 232 at a rotation bearing 240, which allows the control rod 232 to be rotated by the rotatable actuator 212 without being prevented from rotation by the slidable actuator 210 and carriage 242 (which do not rotate).

The carriage 242 is also connected to a wire latch 244, or may be integrally formed therewith. The wire 222 is disposed within the hollow control rod 232 and extends from coupler 220 through the carriage 242 and the wire latch 244. The wire latch 244 is engaged with the second end of the wire 222a. In an example, the wire latch 244 may include two or more clamping surfaces (depicted at 246) that pinch and hold the wire 222. In another example, the wire latch 244 may alternatively (or also) engage an enlarged ferrule 248 that is secured to the wire 222. One or more detents 250, as described below, may engage the wire latch 244 when the wire latch 244 is in a predetermined position, which allows the wire 222 to be released. With this structures in mind, implantation of the localization element 216 is described in further detail with reference to FIGS. 3A-3C.

More specifically, FIG. 3A-3C depict the localization element 216 in retracted, partially extended, and fully-extended positions. In the retracted position of FIG. 3A, no portion of the localization element 216 extends beyond the tip 206 of the cannula 204. In this position, the cannula 204 is inserted into the breast tissue by the interventional radiologist. Also in this position, the slidable actuator 210 is in a first position at a first end of the slot 214 (depicted in FIGS. 2A-2C). Somewhat similarly, the rotatable actuator 212 is disposed at a first end of the spline 238 on the control rod 232. With the slidable actuator 210 in this position, the wire latch 244 is disengaged from the detents 250 and completely engaged with and holding the wire 222. From this first position, the slidable actuator 210 may be advanced in a forward direction F, for example, by a pushing action by the radiologist, to an intermediate position such as depicted in FIG. 3B. As the slidable actuator 210 is advanced, the control rod 232 slides forward so as to apply a corresponding force against the coupler 220, thus advancing the localization element 216 out of the tip 206 of the cannula 204. In FIG. 3B, the localization element 216 is partially extended from the cannula 204. As the localization element 216 projects from the tip 206, the curling of the localization element 218, due to manufacture with a shape-memory material, is apparent. This curling allows the localization element 216 to substantially surround or penetrate the lesion, and prevents migration of the localization element 216 within the tissue of the breast. In this position, the advancement of the control rod 232 repositions the spline 238 relative to the rotatable actuator 212. Also, since the slidable actuator 210 is rigidly fixed to the carriage 242 and wire latch 244, these components are also advanced.

From the partially extended position of FIG. 3B, the slidable actuator 210 may be further advanced (to the position of FIG. 3C) or reversed (to the position of FIG. 3A).

The decision of whether to advance or reverse the localization element 216 is made by the radiologist by viewing the ultrasound display and determining if the localization element 216 is properly positioned relative to the lesion. If advanced in the forward direction F, one or more ramps 252 on the wire latch 244 contact the one or more detents 250 within the body 202. Further advancement in the forward direction F moves the ramps 252 along the detents 250 until the detents 250 reach stops 254, at which point, the wire latch 242 is open, thereby releasing the wire 222, and thus the entire localizer 218. Thus, the localization device 200 includes components disposed therein that only release the localizer 218 when those components reach a certain condition. As such, accidental release of the localizer (e.g., by accidental actuation of a button or release, is prevented). This release condition is depicted in FIG. 3C.

However, if the slidable actuator 210 is moved in a reverse direction R, the configuration of the actuation system 208 allows the localization element 216 to be retracted with single-handed operation. The engagement between the wire latch 242 and the wire 222 (either directly at the clamping surfaces 426 or at the ferrule 248) applies a pulling force to the wire 222, thus allowing the localization element 216 to be retracted. The second end 222a of the wire 222 is simply moved rearward in the wire chamber 228. Thus, the localization device 200 allows for single-handed advancement and retraction of the localization element 216 via simple linear movement of a single element, the slidable actuator 210.

FIG. 3C depicts the fully extended position of the localization element 216, where the localization element 216 is almost or entirely external to the tip 206. The position of the detents 250 engaged within the stops 254 may provide a tactile feedback to the user that the localization element 216 is fully extended. In this position, the slidable actuator 210 is in a second position at a second end of the slot 214. Similarly, the rotatable actuator 212 is disposed at a second end of the spline 238 on the control rod 232. Further, with the detents 250 resting in the stops 254 of the wire latch 242, the wire latch 242 automatically releases the wire 222. Thus, the present localization device 200 does not require any additional manipulation by the surgeon to release the localizer 218 after insertion. The surgeon simply moves the actuator 210 through its complete range of motion so as to release the localizer 218 automatically. At this point, the localization device 200 may be physically withdrawn W from the tissue. In doing so, the second end 222a of the wire 222 slides entirely through the wire latch 244, carriage 242, bearing 240, control rod 232, and cannula 204 so as to be released from the localization device 200. The hooked localization element 216 retains the localizer 218 relative to and within the tissue; any portion of wire 222 disposed outside of the breast may be taped or otherwise secured to the skin until further procedures are performed.

Figure 4A:
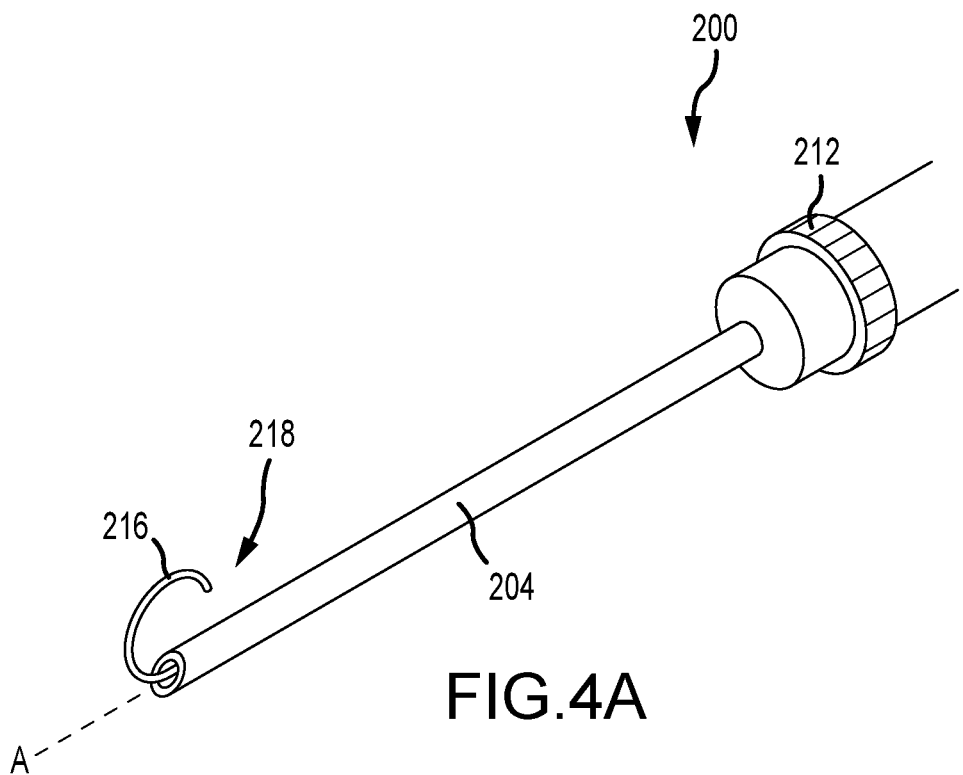
FIGS. 4A-4B depict partial perspective views of the localization device of FIGS. 2A-2C being used in a rotation procedure of a localizer.
Figure 4B:
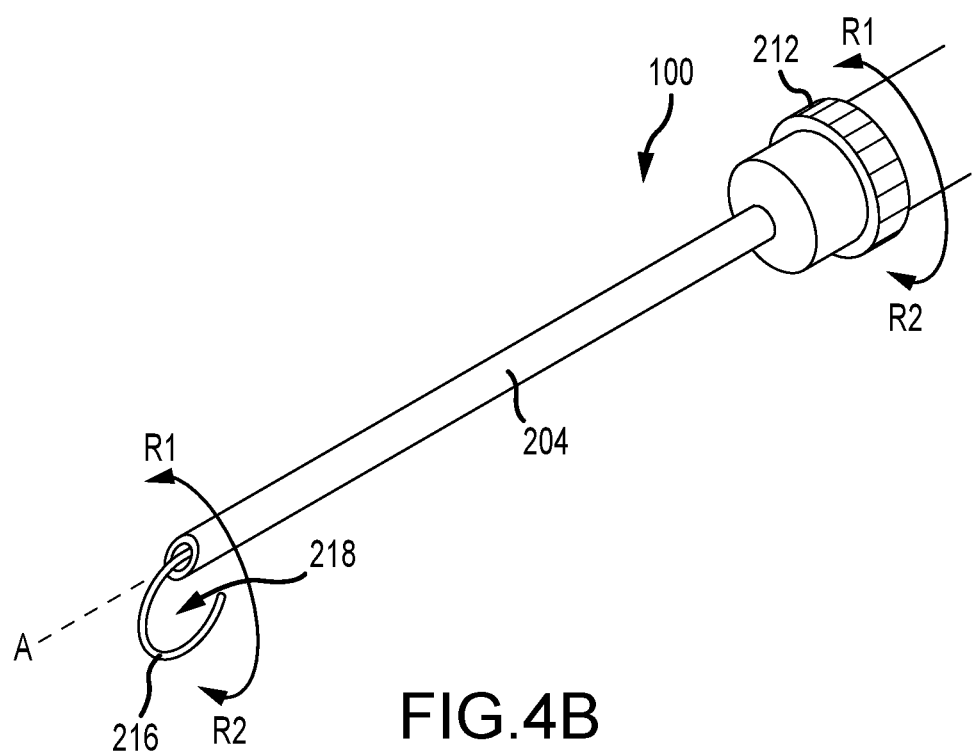

During the localization procedures described above and elsewhere herein, the radiologist may determine that the localization element 216 is being extended in an undesirable orientation relative to the lesion. In such a case, it may be desirable to change orientation of the localization element 216 such that proper curving (e.g., around the lesion or in an orientation so as to achieve the best available visualization) is achieved. With prior art localization devices, this would necessitate rotating the localization device within the palm of the hand, or rotating the entire hand, so as to desirably position the localization element for proper curvature. However, rotation of the device may place a slidable actuator thereof out of reach, while rotation of the hand may be uncomfortable. The localization device 200 depicted herein, however, allows for a rotation procedure of the localization marker 216 separate from rotation of the device 200 itself. In practice, the radiologist may be extending the localization element 216 from the cannula 202 (for example, as depicted in FIG. 4A). The radiologist may determine, based on the images obtained by the simultaneous imaging, that the localization element 216 is curving in an undesirable direction. The radiologist may return the slidable actuator 210 to the position depicted in FIG. 3A. At that time, the radiologist may then rotate the rotatable actuator 212, which again is engaged with the spline 238 of the control rod 232 so as to rotate therewith. The control rod 232 is engaged with the coupler 220 via the key 234/slot 236 arrangement. Thus, rotation of the control rod 232 causes a corresponding rotation of the coupler 220 and localization element 216. Thus, the localization element 216 is able to rotate about the common elongate axis A of the body 202 and cannula 204, while the body 202 and cannula 204 are held in a substantially rotationally static position. As depicted in FIG. 4B, rotation R1 in a first direction rotates the localization element 216 in a corresponding direction. Rotation R2 in an opposite second direction rotates the localization element 216 in a corresponding opposite direction. Regardless, FIG. 4B depicts that the localization element 216 may be completely rotated up to and beyond 360 degrees about the common elongate axis A. Moreover, while FIG. 4B depicts rotation while the localization element 216 is nearly fully extended, this is for illustrative purposes only. To protect adjacent tissues from damage and to prevent undesirable twisting of the localization element 216, rotation of the localization element 216 will ordinarily take place when the localization element 216 is fully (or nearly fully) contained within the cannula 204.

Figure 5A:
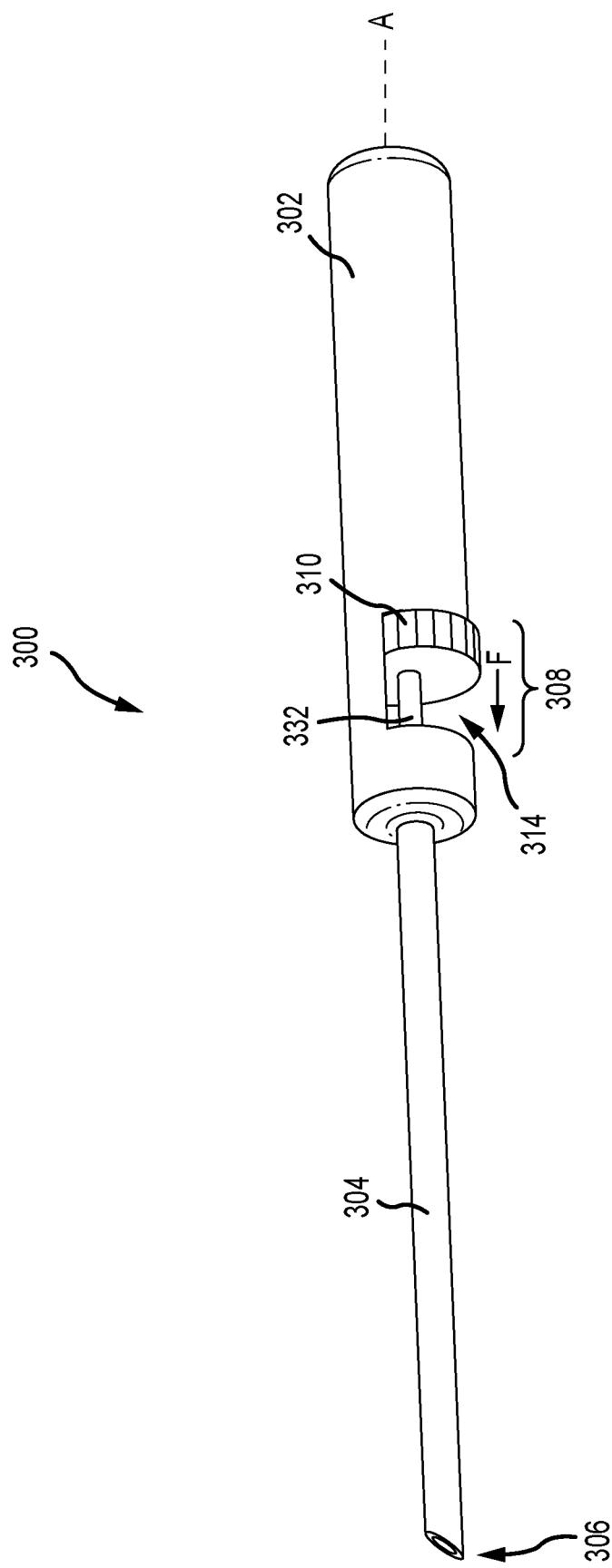
FIGS. 5A-5C depict perspective views of another example of a localization device, being used during an insertion procedure of a localizer.
Figure 5B:
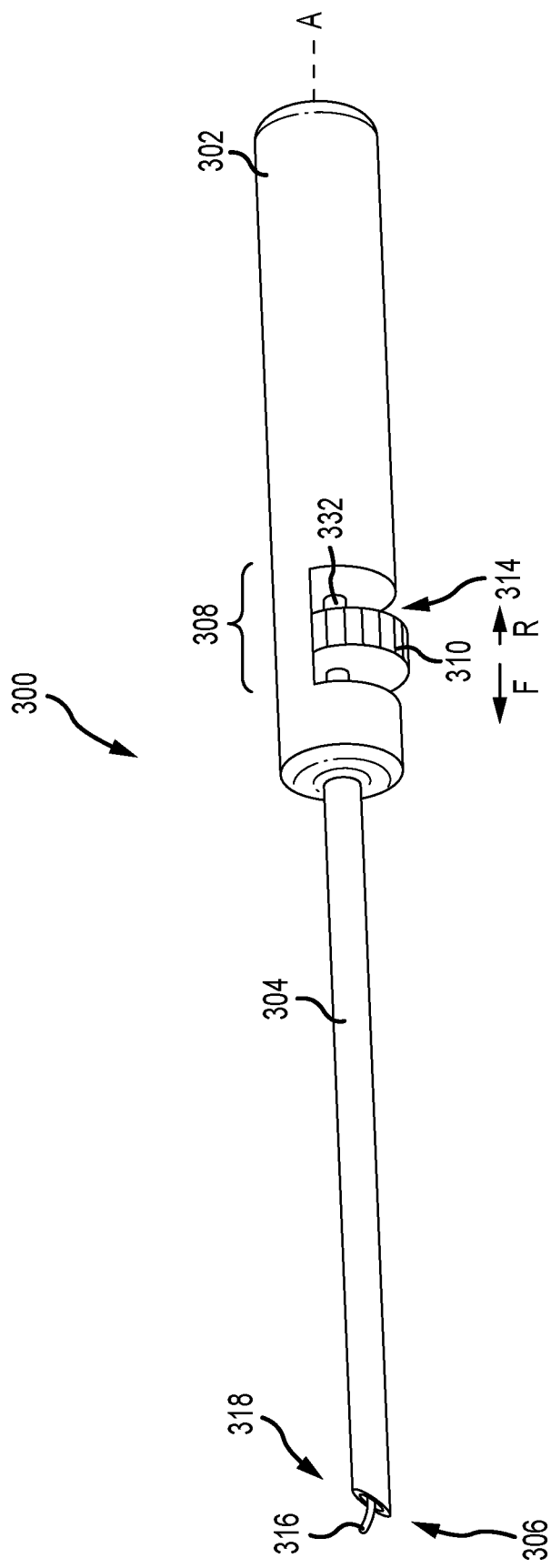
Figure 5C:
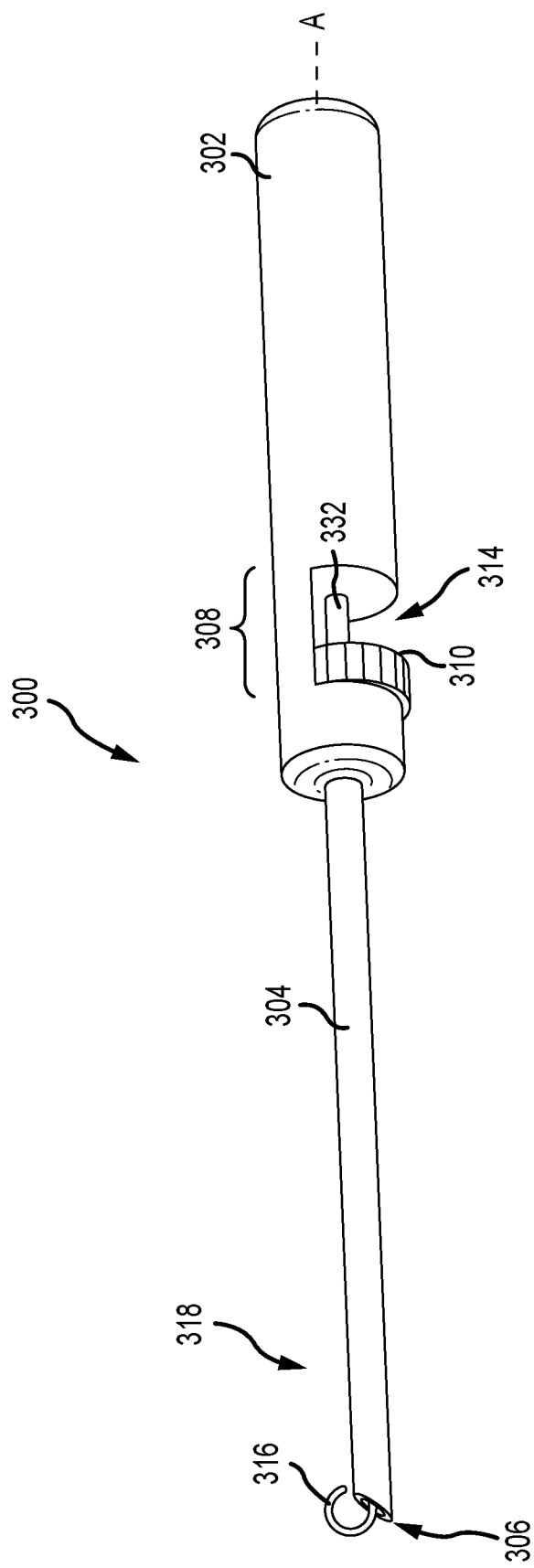

FIGS. 5A-5C depict perspective views of another example of a localization device 300, at various stages of localization element 316 insertion. FIGS. 5A-5C are described concurrently. The device 300 includes a handle or body 302, which is elongate and sized to be gripped in one hand. The body 302 may be formed of a rigid plastic that displays the same characteristics and performance as the localization device 200. A cannula 304 extends from the body 302 such that the cannula 304 and the body 302 define a common elongate axis A. The cannula 304 includes a tip 306 that is angled for penetration of tissue. The localization device also includes an actuation system 308 that differs from the actuation system 208 described above, in that a single actuator 310 that performs two functions (sliding and rotating) is utilized. The actuator 310 is disposed so as to slide along the length of a wide slot 314 defined by the body 302. The actuator 310 is further configured so as to rotate about the axis A, and may be shaped as a generally ring-shaped element, a portion of which may be accessed via the slot 314. The actuator 310 may be knurled or otherwise textured to increase frictional contact with the thumb or finger. Other components of the actuation system 308 include a control rod 332 that is fixed to the actuator 310 so as to responsively slide or rotate based on a corresponding manipulation of the actuator 310. In general, the actuation system 308 is utilized to advance, retract, and/or otherwise move and manipulate a localization element 316 contained within the localization device 300 prior to insertion. The localization element 316 partially depicted in FIGS. 5A-5C may be configured similar to the localization element depicted elsewhere herein, or otherwise configured. The distance that the localization element 316 extends out of the tip 306 of the cannula 304 corresponds generally to the position of the actuator 310, movement of which is bounded by the limits of the slot 314.

FIG. 5A-5C depict the localization element 316 in retracted, partially extended, and fully-extended positions. Internal components of the localization device 300 are similar to those depicted in the localization device 200 above. As such, internal components are not necessarily described in detail. In the retracted position of FIG. 5A, no portion of the localization element 316 extends beyond the tip 306 of the cannula 304. In this position, the cannula 304 is inserted into the breast tissue by the interventional radiologist. Also in this position, the actuator 310 is in a first position at a first end of the slot 314. From this first position, the actuator 310 may be advanced in a forward direction F, for example, by a pushing action by the radiologist, to an intermediate position such as depicted in FIG. 5B. As the actuator 310 is advanced, the control rod 332 applies a corresponding force against the localization marker 316, typically via a coupler (not shown), thus advancing the localization element 316 out of the tip 306 of the cannula 304. In FIG. 5B, the localization element 316 is partially extended from the cannula 304. As the localization element 316 projects from the tip 306, the curling of the localization element 316 is apparent.

From the partially extended position of FIG. 5B, the actuator 310 may be further advanced (to the position of FIG. 5C) or reversed (to the position of FIG. 5A). The decision of whether to advance or reverse the localization element 316 is made by the radiologist by viewing the ultrasound display and determining if the localization element 318 is properly positioned relative to the lesion. FIG. 5C depicts the fully extended position of the localization element 316, where the localization element 316 is almost or entirely external to the tip 306. In this position, the localizer has been released from the internal components such as those described above and such that the hooked localization element 316 retains the localizer 318 within the tissue.

Figure 5D:
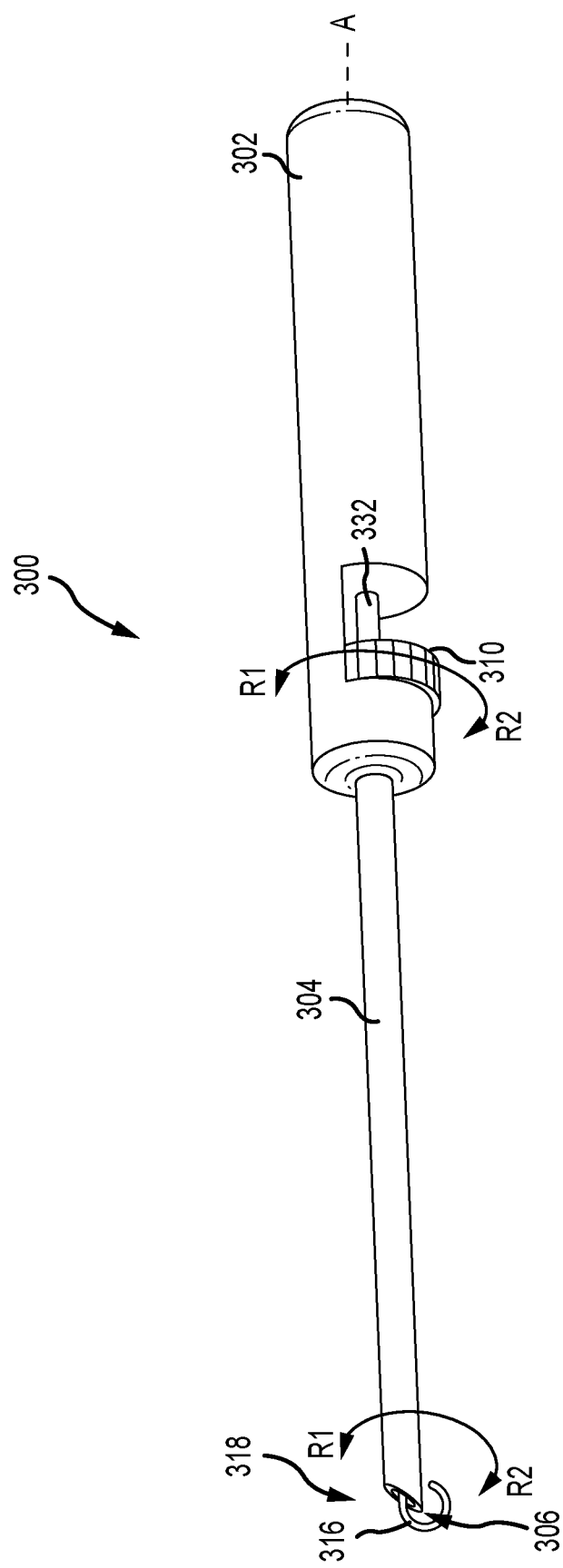
FIG. 5D depicts a perspective view of the localization device of FIGS. 5A-5C being used in a rotation procedure of a localizer.

As described above, during a localization procedure, the radiologist may determine that the localization element 316 is positioned so as to not be curving as required or desired relative to the lesion. In such a case, the localization device 300 allows for a rotation procedure of the localization element 316 separate from rotation of the device 300 itself. In practice, once the radiologist determines that the localization element 316 is curving in an undesirable direction, the radiologist may return the actuator 310 to the position depicted in FIG. 5A. Thereafter, the radiologist may then rotate the actuator 310, which again is fixed to the control rod 332 so as to rotate therewith. As with the localization device 200 of the above figures, the control rod 332 is engaged with a coupler connected to the localization element 316 via the key/slot arrangement. Thus, rotation of the control rod 332 causes a corresponding rotation of the coupler and localization element 316. Thus, the localization element 316 is able to rotate about the common elongate axis A of the body 302 and cannula 304, while the body 302 and cannula 304 are held in a substantially rotationally static position. As depicted in FIG. 5D, rotation R1 in a first direction rotates the localization element 316 in a corresponding direction. Rotation R2 in an opposite second direction rotates the localization marker 316 in a corresponding opposite direction. Regardless, FIG. 5D depicts that the localization element 316 may be completely rotated up to and beyond 360 degrees about the common elongate axis A. Moreover, while FIG. 5D depicts rotation while the localization element 316 is nearly fully extended, this is for illustrative purposes only. To protect adjacent tissues from damage and to prevent undesirable twisting of the localization element 316, rotation of the localization marker 316 will ordinarily take place when the localization element 316 is fully (or nearly fully) contained within the cannula 304.

Figure 6:
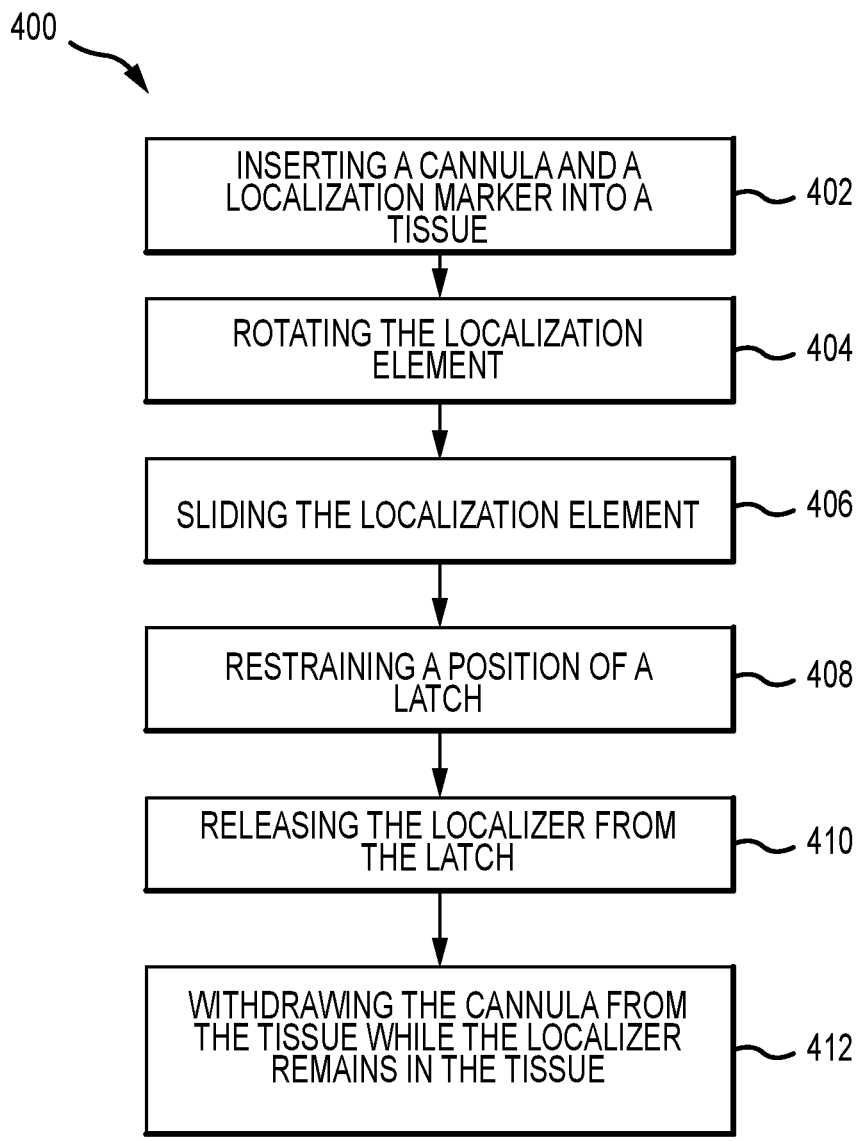
FIG. 6 depicts a method of inserting a localizer with a localization device.

FIG. 6 depicts a method 400 of inserting a localizer with a localization device. The localization device may be one of the examples depicted above or may be manufactured in accordance with the teachings herein. The method 400 begins with inserting a cannula and the localization element into a tissue of a patient, operation 402. The cannula and localization element are inserted into the tissue substantially simultaneously because the localization element is disposed within the cannula as the radiologist holds the body of the localization device and inserts the cannula into the tissue. The cannula has an elongate cannula axis that in certain examples, may be coaxial with an axis of the body. The method continues with rotating the localization element about the cannula axis while holding the cannula in a substantially rotationally static position, operation 404. In the context of this specification, the term "substantially rotationally static" refers to conditions where the radiologist is using an actuator such as those described above to rotate the localization element while the body and cannula of the localization device remain relatively still. As noted above, prior art devices require rotation of the entire localization device in order to cause a corresponding rotation of the localization element. A radiologist with knowledge of the prior art would recognize that rotation of the localization element with the localization devices described herein may be accomplished by rotating the entire localization device in the hand (consistent with the prior art) as well as rotating the localization element while the localization device remains relatively still (a characteristic unique to the described localization devices). In the latter rotation, the localization device is held relatively still, in other words, "substantially rotationally static." Returning to operation 404, typically this is performed while the localization element is still disposed in the cannula, so as to limit the potential of the localization element being rotated against the tissue. As such, rotating the localization element is performed prior to sliding of the localization element (described below). However, given the relative size of the cannula and the localization element, there may be instances where the localization element may be rotated while it protrudes slightly from the tip of the cannula.

In operation 406, sliding of the localization element along the cannula axis while holding the cannula in a substantially slidingly static position is performed. As with the rotational terminology used above, a person of skill in the art would recognize what is meant by "a substantially slidingly static position." Once the localization element has been slid to a predetermined position, restraining a position of a latch within the insertion device, operation 408, is performed. Additionally, and in certain examples, substantially simultaneously with operation 408, releasing the localization element from the wire latch disposed within the insertion device occurs at operation 410. In general, these two previous operations occur prior to withdrawing the cannula from the tissue. The method is complete upon performance of operation 412, withdrawing the cannula from the tissue such that the localization element remains within the tissue, is performed.

This disclosure describes some embodiments of the present technology with reference to the accompanying drawings, in which only some of the possible embodiments were shown. Other aspects may, however, be embodied in many different forms and should not be construed as limited to the embodiments set forth herein. Rather, these embodiments were provided so that this disclosure was thorough and complete and fully conveyed the scope of the possible embodiments to those skilled in the art.

Although specific embodiments are described herein, the scope of the technology is not limited to those specific embodiments. One skilled in the art will recognize other embodiments or improvements that are within the scope and spirit of the present technology. Therefore, the specific structure, acts, or media are disclosed only as illustrative embodiments. The scope of the technology is defined by the following claims and any equivalents therein.

What is claimed is:

1. A localization device comprising:
   a body having a first end and a second end;
   a cannula extending from the second end of the body, wherein the cannula defines a cannula axis and the cannula is rigid;
   an actuation system disposed on a lateral body portion of the body between the first end and the second end, wherein the actuation system includes a slidable actuator configured to move along the cannula axis and a rotatable actuator configured to rotate about the cannula axis; and
   a control rod slidably and rotatable disposed within at least one of the body and the cannula, wherein the control rod includes a first end and an opposite second end, the first end of the control rod is disposed within the cannula and the second end of the control rod includes a spline coupled to the slidable actuator of the actuation system, wherein the rotatable actuator is slidably mounted at the spline such that the slidable actuator is configured to slide the control rod relative to the rotatable actuator and along the cannula axis, and the rotatable actuator is configured to rotate the control rod around the cannula axis.

2. The localization device of claim 1, wherein the slidable actuator is discrete from the rotatable actuator.

3. The localization device of claim 1, wherein the actuation system is configured to be operated with one hand.

4. The localization device of claim 1, wherein a portion of the rotatable actuator protrudes from the lateral body portion of the body between the first end and the second end.

5. The localization device of claim 1, further comprising:
   a localization marker releasably coupled to the control rod, wherein the localization marker is configured to slide along the cannula axis due to a sliding movement of the control rod, and wherein the localization marker is configured to rotate relative to the cannula axis due to a rotating movement of the control rod.

6. The localization device of claim 5, wherein the localization marker comprises a localization element and a flexible material coupled to the localization element, wherein the flexible material is disposed at least partially within the control rod.

7. The localization device of claim 6, further comprising a coupler connecting the localization element to the flexible material.

8. The localization device of claim 6, wherein at least a portion of the flexible material is curved within the body.

9. The localization device of claim 6, wherein the flexible material includes a wire.

10. The localization device of claim 6, wherein the localization element includes a hook or a double hook.

11. The localization device of claim 1, wherein the actuation system comprises a latch, wherein the localization device further comprises:
    a localization element coupled to the actuation system and configured for movement about the cannula axis and along the cannula axis; and
    a flexible material coupled to the localization element, and wherein the flexible material is releasably coupled to the latch.

12. The localization device of claim 11, wherein the rotatable actuator is discrete from the slidable actuator.

13. The localization device of claim 11, wherein the actuation system is positionable in a first position and a second position, and wherein the latch is configured to disengage from the flexible material when the actuation system is in the second position.

14. The localization device of claim 13, wherein when in the second position, the localization element is fully extended from the cannula.

15. The localization device of claim 1, wherein the lateral body portion of the body between the first end and the second end defines a slot.

16. The localization device of claim 15, wherein the slidable actuator is disposed so as to slide along the length of the slot on the lateral body portion of the body between the first end and the second end.

17. A localization device comprising:
    a body having a first end and a second end defining a longitudinal axis, the body defining a slot extending along the longitudinal axis on a lateral body portion between the first end and the second end;
    a cannula extending from the second end of the body, wherein the cannula defines a cannula axis co-axial with the longitudinal axis and the cannula is rigid;
    an actuation system disposed on the lateral body portion of the body, wherein the actuation system includes a single actuator disposed at least partially within the slot, the single actuator configured to both slidably move along the cannula axis and rotate about the cannula axis; and
    a control rod slidably and rotatable disposed within at least one of the body and the cannula, wherein the control rod is operatively coupled to the single actuator such that the control rod also both slides and rotates relative to the cannula axis.

18. The localization device of claim 17, further comprising:
    a localization marker releasably coupled to the control rod, wherein the localization marker is configured to slide along the cannula axis due to a sliding movement of the control rod, and wherein the localization marker is configured to rotate relative to the cannula axis due to a rotating movement of the control rod.

19. The localization device of claim 18, wherein the localization marker comprises a localization element and a flexible material coupled to the localization element, wherein the flexible material is disposed at least partially within the control rod.

* * * * *